United States Patent
Griguol (10) Patent No.: US 9,427,296 B2
(45) Date of Patent: Aug. 30, 2016

(54) MICRO SLING AND IMPLANTATION TOOL FOR URINARY INCONTINENCE AND FAECAL INCONTINENCE TREATMENT

(75) Inventor: Osvaldo Nicolas Griguol, Cordova (AR)

(73) Assignee: PROMEDON S.A., Cordova (AR)

( * ) Notice: Subject to any disclaimer, the term of this patent is extended or adjusted under 35 U.S.C. 154(b) by 892 days.

(21) Appl. No.: 12/664,078

(22) PCT Filed: Jun. 12, 2007

(86) PCT No.: PCT/IB2007/001577
§ 371 (c)(1),
(2), (4) Date: Jun. 4, 2010

(87) PCT Pub. No.: WO2008/152435
PCT Pub. Date: Dec. 18, 2008

(65) Prior Publication Data
US 2010/0256443 A1 Oct. 7, 2010

(51) Int. Cl.
*A61F 2/00* (2006.01)
(52) U.S. Cl.
CPC ...... *A61F 2/0045* (2013.01); *A61F 2220/0016* (2013.01)
(58) Field of Classification Search
CPC .......... A61B 17/064; A61B 17/06109; A61B 17/0401; A61B 2017/00805; A61B 2017/0412; A61B 2017/0427; A61B 2017/0464; A61B 2017/0647; A61B 2017/0461; A61F 2/0045; A61F 2220/0016
USPC .................................................. 600/30, 37
See application file for complete search history.

(56) References Cited

U.S. PATENT DOCUMENTS

| 2004/0144395 A1* | 7/2004 | Evans et al. ............... 128/885 |
| 2004/0231678 A1* | 11/2004 | Fierro ...................... 128/885 |
| 2005/0267325 A1* | 12/2005 | Bouchier et al. ........... 600/37 |
| 2006/0015069 A1 | 1/2006 | Evans et al. |
| 2006/0089524 A1* | 4/2006 | Chu ........................... 600/37 |
| 2006/0195007 A1* | 8/2006 | Anderson et al. .......... 600/29 |
| 2006/0195010 A1 | 8/2006 | Arnal et al. |
| 2006/0195011 A1 | 8/2006 | Arnal et al. |
| 2006/0229596 A1* | 10/2006 | Weiser et al. ............... 606/37 |
| 2007/0055095 A1* | 3/2007 | Chu et al. ................... 600/37 |
| 2009/0306464 A1 | 12/2009 | Griguol |

FOREIGN PATENT DOCUMENTS

| WO | 03 002027 | 1/2003 |
| WO | 2006 045042 | 4/2006 |

OTHER PUBLICATIONS

Communication pursuant to Article 94(3) EPC dated Mar. 14, 2013 in EU Patent Application No. 07 7890417.8-1662.

* cited by examiner

*Primary Examiner* — Navin Natnithithadha
*Assistant Examiner* — Kaylee Wilson
(74) *Attorney, Agent, or Firm* — Oblon, McClelland, Maier & Neustadt, L.L.P.

(57) ABSTRACT

Sling for urinary and fecal incontinence treatment comprises a mid-part 2, at least two fixing tails 3 provided with a anchoring means and comprising an elongated part 7, fixed to the mid-part 2, and an end part 4 fixed to the elongated part 7. The end part 4 includes a connection means 6 connectable to a tool. At least one fixing tail 3 is a autofixing tail including self-anchoring means 30, 31, 32, 33. The two elongated parts are flat and the end parts are axially disconnectable from the tool. The flat elongated part of the autofixing tail comprises flat self-anchoring means.

10 Claims, 9 Drawing Sheets

MICRO SLING AND IMPLANTATION TOOL FOR URINARY INCONTINENCE AND FAECAL INCONTINENCE TREATMENT

This invention refers to a micro sling to treat female urinary and faecal incontinence. In particular, the invention relates to sling comprising a central mesh joined by anchoring tails designed to anchor into tissues of a body.

Urinary incontinence affects many people, especially men after prostatectomy and women. Four types of urinary incontinence have been defined by the International Continence Society: stress, urge, overflow and reflex incontinence.

The first and most frequent type is called stress incontinence, which takes place during straining, following laughter or cough, or while exercising. It results from weakness of the urethral sphincter which is no longer capable of sealing the bladder due to the loosening of the muscles of the perineum and/or Intrinsic Sphincter Deficiency (ISD). This form of incontinence can occur after childbirth or at menopause, but it can also affect young sportswomen who overdevelop their abdominal muscles to the detriment of the perineum, or in neurogenic bladder such as myelomeningocele.

The second most frequent form of incontinence, referred to as overactive bladder, results from involuntary contractions of the (hyperactive) bladder which manifests as an excessively frequent and irrepressible urge to urinate.

Some women suffer from mixed incontinence, which is a combination of the forms mentioned above.

Overactive bladder can be cured by taking bladder relaxation medication. For stress incontinence treatment and/or prevention, surgery is often necessary.

The techniques known from the prior art consist in restoring the natural mechanisms of continence; i.e., maintaining the urethra in the abdominal cavity and/or increasing urethral resistance. To do this, a sling under the bladder neck or urethra has already been used.

Sling procedures for the management of female stress urinary incontinence (SUI) have been around for decades, but it was not until last decade that these became the preferred ones. Minimally invasive procedures are the procedures of choice in many centers for their efficacy and low morbidity.

The understanding of the pathophysiological concepts of stress urinary incontinence has consistently improved over the past decade and their applications have led to the development of many surgical techniques.

Based on the Integral Theory, Petros and Ulmsten purposed the Tension-free Vaginal Tape (TVT). This theory claims that midurethral tape may stabilize the urethra during straining without modifying the urethral mobility. One can refer to Petros, P, Ulmsten U "An integral theory and its method for the diagnosis and management of female urinary incontinence". Scand. J. Urol. Nephrol., 153: 1-93, 1993; and to: Ulmsten U, Henriksson L, Johnson P, Varhos G. "An ambulatory surgical procedure under local anesthesia for treatment of female urinary incontinence". Int Urogynecol J, 7:81-86, 1996.

Despite the good cure rate reported with TVT, major complications such as bowel and blood vessel injuries have been described (Petros P E, Richardson P. Midurethral "Tissue Fixation System sling—a Micromethod for cure of stress incontinence-Preliminary Report". Aust NZ J Obstet Gyn 45: 372-375, 2005).

To avoid these complications, alternative approaches using a transobturator needles have been developed (Delorme E—"La bandellette trans-obturatrice: un procede mini-invasif pour traiter l'incontinence urinaire d'effort de la femme. Progrès en Urologie>>, 1:1306-13, 2001). The continence rate with the transobturator approach has been similar to that obtained with the transvaginal retropubic approach. Most of the complications described are related to the blind nature of these procedures.

One such problem is that the needles used for inserting the tape are comparatively large, with needles having, for example, a diameter of around 3-6 mm and a length of around 200 mm. This is also a cause of concern for patients who see these needles before or during the procedure (performed under local anesthesia), and can lead to a high vascular injury rate. Another disadvantage of both, the transobturator and transvaginal retropubic approaches, is that the tape is a relatively large foreign body mass to be retained inside the body which can lead to related inflammation, infection translocation, erosion, fistula and the like.

The patent application WO 03/002027 describes an adjustable, self-anchoring sling for urinary incontinence treatment. This sling comprises a band whose mid-part is perforated. At both sides of the mid-part, there are two columns provided with conical shapes which constitute the self ensuring system. The autofixing columns are 175 mm long and 5 mm diameter. Two needles, with a 3.5 mm diameter, are introduced through the lower abdominal wall and exit first through a vaginal incision. Then, the two columns are connected to a hook at the end of each needle. The two needles are pulled and bring with them the two columns and the mid-part of the sling through the vaginal incision. When the sling is in place, the surgeon introduces scissors through another incision and cuts the extra lengths of the autofixing columns. These extra lengths are removed from the patient body through the two lower abdominal punctures. The fact that the needle has to be removed through the lower abdominal wall is disadvantageous due to the trauma caused to the patient in this area and the pain of said abdominal wounds. The use of the needle in the transobturator approach may produce anatomical damage to nerves and blood vessels.

The patent EP1 324 705 B1 describes to a surgical implant and method for supporting the urethra. The implant comprises a suburethral support suspended between two soft tissue anchors that do not penetrate the lower abdominal wall and are attached to either side of the suburethral support.

The soft tissue anchor requests a movement back to allow wings to open. Once the anchor is in place, the connection of suspending means to sub-urethral support is modified to get the suitable length towards the anchors. Once the anchors are in place, the connection between the sub-urethral support and the suspending means are modified in order to get the suitable length of suspension between the sub-urethral support and the anchors. This modification of the connection, when the sub-urethral support is in place, is a complex operation.

Faecal incontinence is now known to affect between two and seven percent of the healthy adult population. For patients with faecal incontinence due to simple external sphincter damage, overlap repair provides a good short term outcome in most. However longer term follow up has been disappointing. Those patients with smooth muscle internal sphincter defects or degeneration, or external sphincter weakness or complex disruption, are not amenable to simple repair (Leroi A M, Kamm M A, Weber J, Denis P, Hawley P R. Internal anal sphincter repair. Int J Colorect Dis 1997; 12; 243-245). While some patients are helped by antidiarrhoeal drugs such as loperamide or codeine phosphate, this is not a satisfactory long term solution for most patients.

Injection of sphincter bulking agents to close down the anal canal has been reported to provide some relief in the short term but migration or displacement of the injected product seems to occur with time. Radiofrequency induced scarring has not had impressive results to date. Irrigation to clear the rectum is a time consuming procedure suitable only for the most compliant patients.

Major interventions such as the dynamic gracioplasty or the newer artificial bowel sphincter provide an elevation in resting pressure. These would seem appropriate in cases of severe incontinence but require considerable expertise to achieve a good result and are associated with a relatively high complication rate (Sielezneff I, Malouf A J, Bartolo D C C, Pryde A, Douglas S. Dynamic Gracioplasty in the treatment of patients with faecal incontinence. Brit J Surg 1999; 86:61-65). A further therapy for patients with sphincter dysfunction is sacral nerve stimulation but the exact indications for its use in faecal incontinence have yet to be defined.

One look for a simple treatment for faecal incontinence due to sphincter insufficiency. Any device would have to be easy to insert, have a low complication rate and withstand the scrutiny of time.

The patent application WO 2005/082275 describes a passive, incontinence-inhibiting prosthesis for insertion into a position substantially coaxial with and at least partially surrounding at least a portion of the anal canal.

The patent application US 2007/0021650 describes an assembly for treating faecal incontinence comprising: an elongate needle that is sized and shaped to be initially inserted through and abdominal incision and to then emerge from at least one other incision and a sling for implantation in the body during the faecal incontinence procedure.

There is a need to propose a sling for urinary or faecal incontinence treatment, an implantation tool, an implantation system, an implantation method and particular uses of a sling which reduce the above mentioned drawbacks. In particular, an aim is to reduce the invasion due to the implantation procedure and tools, to provide similar holding effect of the patient organ, while the trauma is reduced. It reduces the need to modify the sling once it is in place. For example, there in no need to introduce scissors to cut extra lengths of the fixing columns, or there is no need to modify the connection between suspending means and sub-urethral support once the anchoring system is in place.

According one embodiment, the sling for urinary and faecal incontinence treatment comprises a mid-part, at least two fixing tails provided with a anchoring means and comprising an elongated part fixed to the mid-part, and an end part fixed to the elongated part. The end part includes a connection means connectable to a tool. At least one fixing tail is a autofixing tail including self-anchoring means. The two elongated parts may be substantially flat and the end parts are axially disconnectable from the tool. The flat elongated part of the autofixing tail may comprise substantially flat self-anchoring means.

Flat elongated part may include holes or bumps or the like. Substantially flat elongated part is understood as having a thickness lower than a width.

In such a sling, the flat shape of the elongated part allows to introduce an implantation tool simultaneously with a sling through the same incision. The implantation tool, for example a needle, can be located on the flat side of the elongated part of the fixing tail. The connection means allows the needle to push the end part and bring the fixing tail side by side with the needle. There is no loosen space between the needle and the elongated part of the fixing tail. The fact that the self anchoring means is flat make it compatible with an implantation of the sling by a pushing procedure. Once the first fixing tail is in place, the connection means can be axially disconnected. The needle can be removed by the same incision. The first fixing tail stay in place due to the anchoring means. Compared with the sling described in WO03/002027, the sling reduces the number of punctures requested for the implantation.

In addition, the auto fixing tail can be introduced in the same way by pushing the implantation tool. The self anchoring means provide an axial retention without pulling back the tail. Therefore, the auto fixing tail can be pushed up to its final location. There is no need to modify any length of the sling after the implantation. Additionally, the fact that, at least the self anchoring means is included in the elongated part of the auto fixing tail gives the opportunity to use the length of that elongated part to provide retention. It gives a very efficient anchoring without extra space needed at the end of the tail. Compared with the sling described in EP 1 324 705, it simplifies the implantation procedure and reduces the space requested to implant the sling.

Preferably, the end part and the elongated part of the fixing tail are made of the same material.

Preferably, the end part includes a butting surface substantially perpendicular to a distal portion of the elongated part.

Preferably, the connection means of the end part includes a fixing hole, substantially parallel to the distal portion of the elongated part. With such axial hole, the implantation tool may have a simple axial tip entering into that hole. With that axial hole, the tool can guide the sling in lateral and in at least one axial direction. It is simple to disconnect the tool from the sling.

Preferably, the thicknesses of the elongated parts are between 0.3 to 1 mm. This small thickness contributes to make it possible to implant that sling by a pushing procedure. For example, the needle may have a 2 mm diameter. The extra thickness added by a thin tail pushed with the needle, is acceptable for implantation in usual patient.

Preferably, the self anchoring means comprising two longitudinal lines of thorn-like projections radially extending from a central part of the tail and having a triangular or a rectangular or a trapezoidal or a curved shape. Such projection give a very efficient retention.

Preferably, the self anchoring means comprises sub units substantially rigid. This provides retention in at least one axial direction as soon as the tail is introduced into a soft tissue.

Preferably, the width of the tails is being between 2 to 5.5 mm, including the lateral sub units or thorn-like projections. Such relatively narrow tail is compatible with a good level of retention when a plurality of sub units or thorn-like projections is distributed along the elongated part.

Preferably, each fixing tails are autofixing tails provided each with self-anchoring means.

Optionally, the mid part is a plan mesh comprising a main part substantially rectangular, and two side tongues, extending from the two end of a little side of the main part into two substantially perpendicular directions, a fixing tail extending from each side tongues. This sling is particularly adapted for posterior vaginal wall prolapse treatment or for vaginal vault prolapse treatment.

Optionally, the main part of the mesh comprises two lateral tongues extending in a direction substantially perpendicular to the large side of the main part, a fixing tail extending from each lateral tongue. This sling is particularly adapted for anterior vaginal wall prolapse treatment.

In another aspect, an implantation tool for urinary or faecal incontinence treatment comprises a cannula, a awl axially movable inside the cannula between a protruding and a non-protruding position, and an actuator of the awl.

Preferably, the awl includes a tip with a stop, the stop diameter being larger than the awl diameter.

In another aspect, an implantation system includes a sling and an implantation tool has a diameter adapted to enter into the fixing hole of the sling, the cannula being designed for not entering into said fixing hole. Such tool is easily disconnectable in an axial direction. When the actuator pulls the awl inside the cannula. The cannula holds in place the end part of the fixing tail. This avoids any unwanted traction when the implantation tool is removed.

Preferably, the fixing hole has a diameter smaller than the stop diameter and elastically deformable to allow the awl tip to cross along the fixing hole, the actuator being designed such that, in the protruding position, the stop protrudes from the end part of the tail. The stop of the awl tip improves the security of the connection between the tool and the sling. It prevents damages coming from unwanted disconnection.

In another aspect, an implantation method of a sling into a soft tissue uses a needle or a trocar, comprising a preliminary step of attaching an end part of the sling to the needle end such way that the attachment holds the sling at least in the tensile direction of the sling. It comprises a further step of pushing the needle and the end part of the sling into the soft tissue, in order to carry the sling with the needle side by side. That method gives the opportunity to introduce the sling and the implantation tool through the same incision, and to remove the tool through the same incision again.

Preferably, the preliminary attachment is such that it holds the sling end part in any direction, the step of pushing the needle or the trocar being performed, up to a place where the sling end part reaches its final location into the soft tissue, and wherein the needle or the trocar is further detached from the sling end part without either pulling or pushing said sling end part.

In another aspect a use of a sling for faecal incontinence treatment comprises a sling mesh supported in a low tension by the external sphincter and self anchoring tails are attached to the anococcygeal ligament and/or to the central perineal tendon. That method can be used with any type of sling. It is of a particular interest when using a small sling with auto fixing tails.

Other features and advantages will appear to the light of the detailed description of some embodiments, as non-restrictive examples and illustrated by the drawing in annex, according to which.

Figure 1:
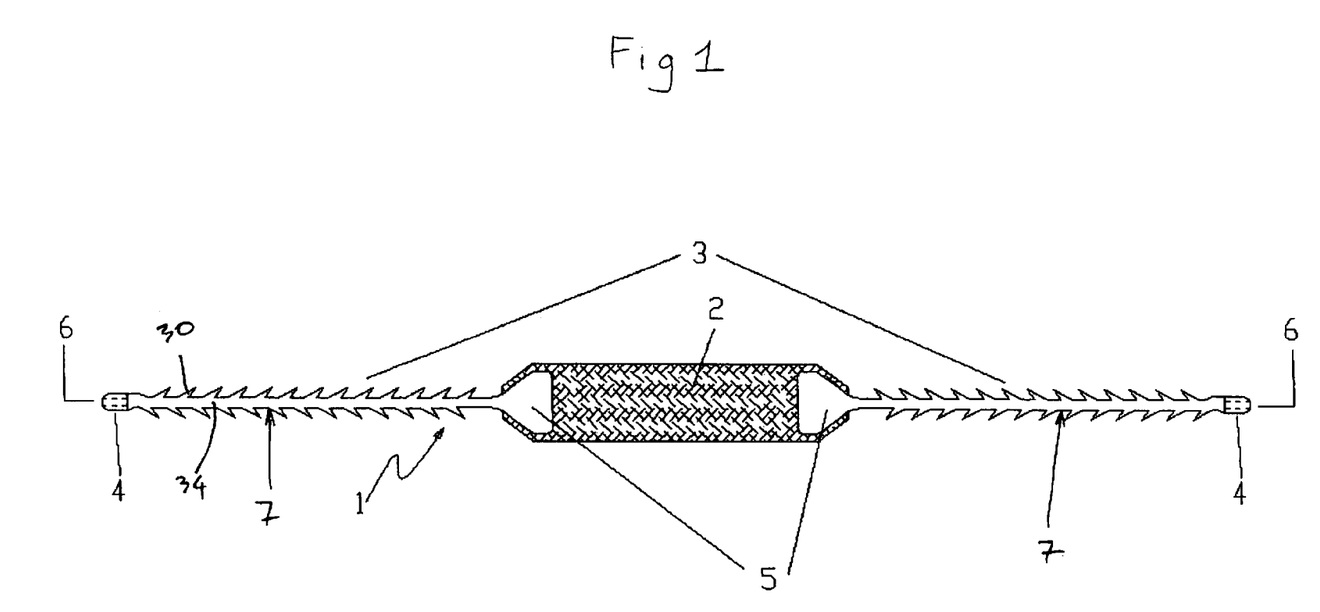
FIG. 1 is a plan view of a sling.

As illustrated in FIG. 1, the sling 1 comprises a mid-part 2 and two fixing tails 3. The fixing tails 3 comprise a fixing pad 5 by which the fixing tails 3 are fixed on the mid part 2. The fixing tail 3 further comprises an end part 4, opposite to the pad 5 and an elongated part 7 between the end part 4 and the pad 5. The end part 6 includes a fixing hole 6 for receiving an implantation tool.

The mid-part 2 has substantially rectangular shape and stretches longitudinally between both ends. This mid-part 2 is design to be implanted under the middle urethra or the bladder neck. The mid-part 2 comprises a mesh with pores or holes which are rapidly covered by the surrounding tissue.

Amongst its holes or perforations interconnective tissue grows between the vaginal flap and the urethra. This leads to a great integration of the implant without loss of vascularization between the bladder and the vagina. As a matter of fact, since there is normal vascularization in the implant integration area, the risk of necrosis and post-operative erosion and infection diminishes.

Optionally, the perforated mid-part 2 is preferably a polypropylene mesh, but it can also be made of other synthetic materials such as polyester, silicone, polyurethane, polyamide, nylon, polytetrafluoroethylene such as Teflon, polyethylene terephthalate, latex or any other thermo-hardened or thermo-formed plastics or gums. In the case of fibrous materials, the latter may be woven or non-woven. Thus, it will be possible to use meshes made of polyester or a mixture of these materials.

In addition, the mid part can be made of biologic materials such as bovine pericardium, different types of collagen, or other animal or human byproducts such as processed fascia lata (Tutoplast®), porcine small intestinal submucosa (STRATASIS™), tissue regeneration matrix (REPLI-FORM™), and the like.

The mid-part 2 may have a length of 20-100 mm, preferably 34 mm; a width of 4-13 mm, preferably 7.5 mm and a thickness of 0.2-2.0 mm, preferably 0.5 mm.

The fixing tails 3 are preferably made of polypropylene, or any other synthetic material such as an ultra high molecular weight polyethylene, a polyurethane, a polytetrafluoroethylene such as Teflon, a polyamide or any other thermosets or thermoplastics.

The fixing tails 3 and the mid-part 2 of the sling are preferably radioopaque, but they can also be radiotranslucent.

The fixation between the pad 5 and the mid-part 2 is possible by means of thermofusion or biocompatible adhesive or surgical suture. The sling used for implantation with the pad already fixed on the mid-part 2. It is design not to be demountable. That fixation is considered as permanent.

The fixing tail 3 comprises a band with two longitudinal lines of thorn-like projections. The two lines of thorn-like projections are arranged at the same level. These are fixed between tissues where the sling is placed and are responsible for keeping the sling in place. The thorn-like projections 30 are placed preferably at different levels though they could also be arranged in a line.

Figure 2:
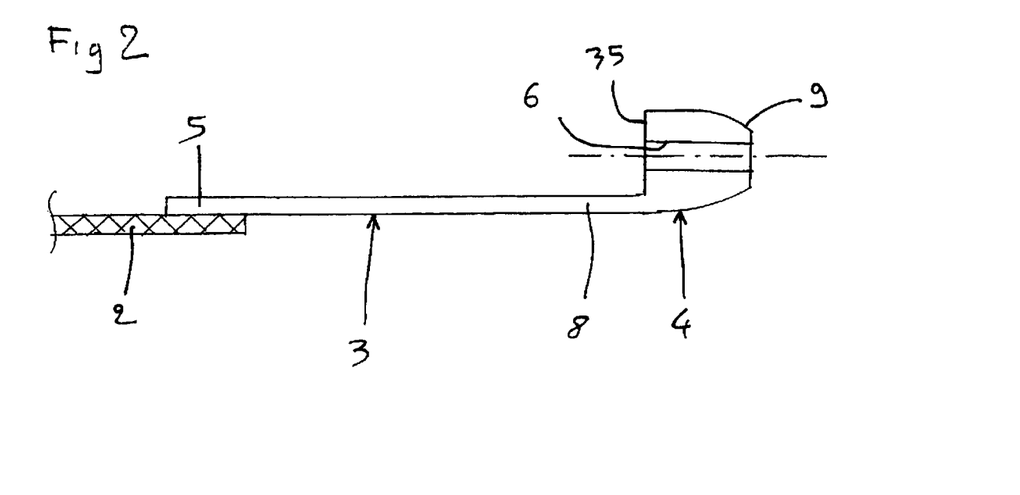
FIG. 2 is a longitudinal section through a sling.

As illustrated in FIG. 2, the end-part 4 is basically cylindrical but it can also be rectangular. The fixing hole 6 is substantially parallel to a distal portion 8 of the elongated part 7. The longitudinal hole 6 is use for threading the surgical instruments for sling implantation. The proximal end of the end part 4, relatively to the mid part 2, is a butting surface 35, substantially perpendicular to the distal portion 8 of the elongated part 7. The distal end of the end part 4 is provided with a chamfer or a round 9.

Figure 3:
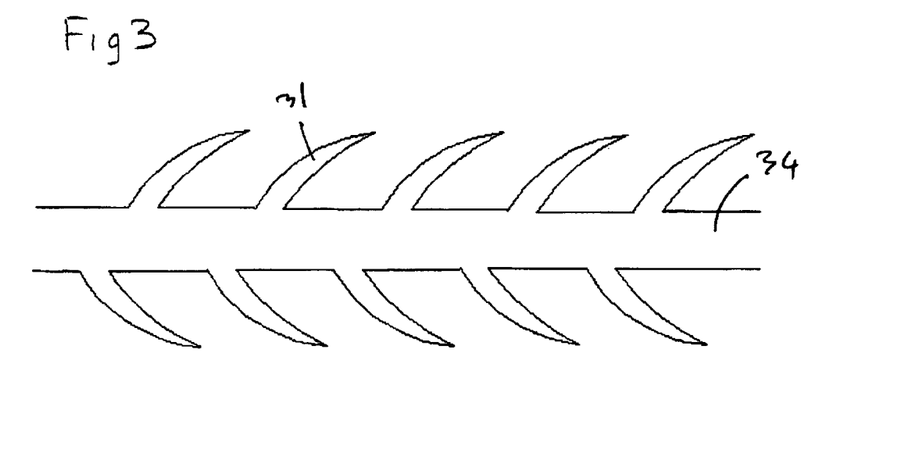
FIGS. 3 to 5 show others self anchoring tails.
Figure 4:
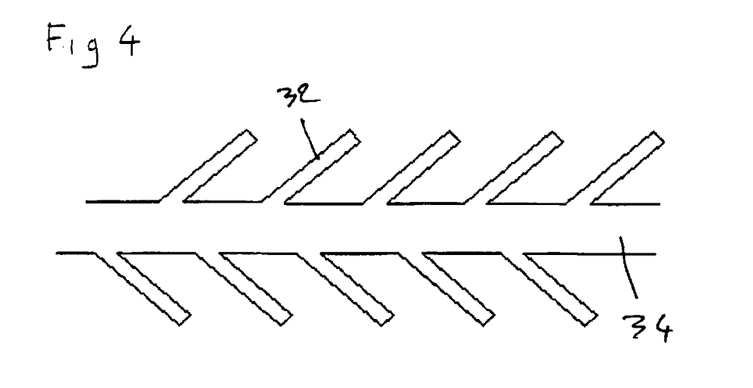
Figure 5:
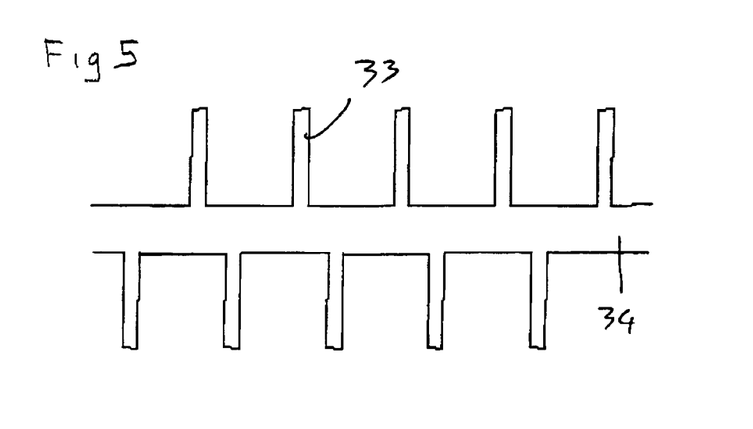

As illustrated in FIGS. 3 to 5, the fixing tail 3 comprises thorn-like projections 30, 31, 32, 33 extending laterally from a central part 34. The thorn-like projections can have various shapes and sizes to achieve different tissue anchoring levels. For this application, triangular thorn-like projections 30 are preferred (FIG. 1). Rectangular in shape thorn-like projections 32, 33 are also acceptable, and the location in the fixing tail 3 can be perpendicular (FIG. 5) or oblique (FIG. 4). Curved hook-like projections 31 (FIG. 3) are another option; these have a high rate of tissue anchoring. These different shapes constitute different anchoring means. They are self-anchoring means because, once introduced into a soft tissue, they provide immediately retention against back movement. There is no need to pull back the tail 3 to provoke such retention. In other words, these tails are auto fixing tails or self anchoring tails.

Self-anchoring tails are 20-55 mm long, preferably 40 mm, 2-5.5 mm large (between projection ends), preferably 3.5 mm, and 0.3-1 mm thick, preferably 0.6 mm (where the thorn-like projections are located). These dimensions correspond to a rectangular body; however, the self-anchoring tail can have somewhat curved ends and thorn-like projections can have rounded borders. Retetion test have been performed in bovine meat. Such fixing tail, introduced with a 2 mm diameter needle, have 890 grames of retention. Much bigger fixing column with conical shapes of 5 mm diameter have shown lower retention.

Figure 6:
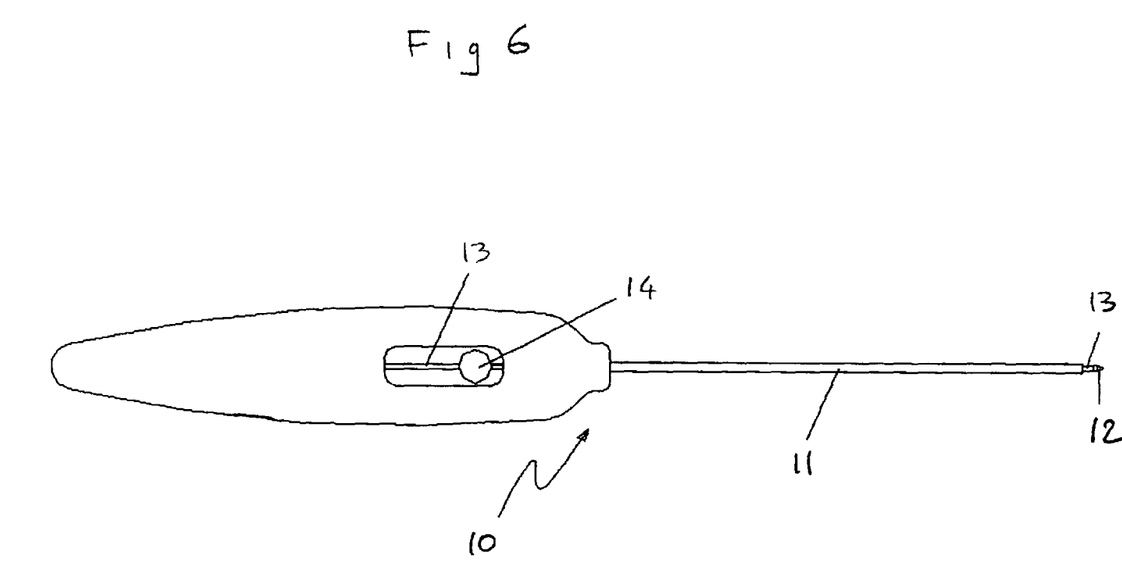
FIG. 6 is a plan view of the mini-trocar.

As illustrated in FIG. 6, micro sling implantation is performed using a mini needle or mini trocar of 1.5-2.5 mm in diameter, preferably 2 mm.

The mini trocar 10 can be straight or curved; however, slightly curved near the end is preferred. It consists of a cannula 11 that is longitudinally crossed by an awl 13 which has a stop 12 in it end. The awl 13 is moved forward or backward by moving a button 14. For sling implantation, the end of the awl 13 is threaded in the end part 4 of the self-anchoring tail 3.

Figure 7:
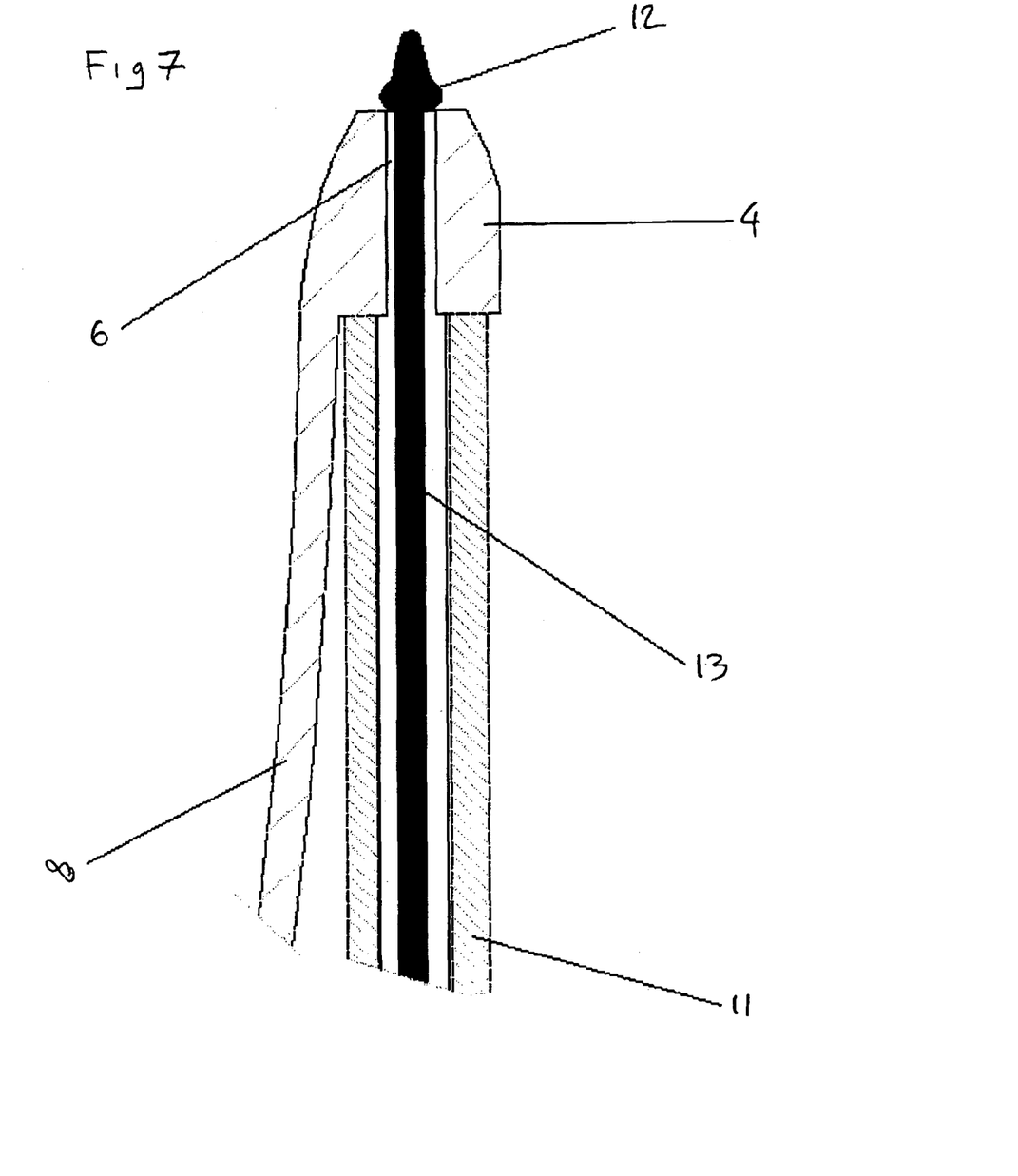
FIG. 7 is a section, illustrating the thread of the end part of tail with the mini-trocar.

As illustrated in FIG. 7, the stop 12 blocks the sling end part 4 allowing for safe handling and avoiding involuntary unthreading. With the mini trocar 10 the self-anchoring tail 3 can be placed in the desired position. Unthreading is performed by moving the button 14 backward. The awl 13 is then axially disconnected from the sling end part 4.

Alternatively, the sling 1 may be pushed into the body with a mini needle (not illustrated). The mini needle has tip, cylindrically depressed in diameter, between 0.5-1.2 mm, preferably 0.9 mm.

Figure 8:
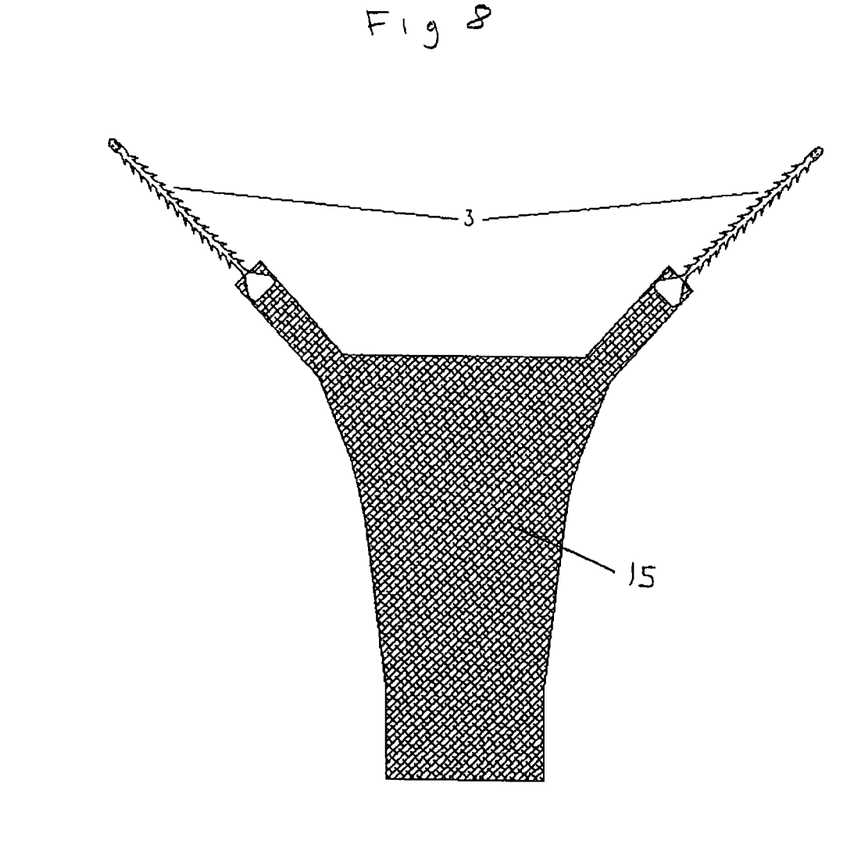
FIG. 8 is a plan view of an implant for posterior vaginal wall prolapse and vaginal vault prolapse treatment.
Figure 9:
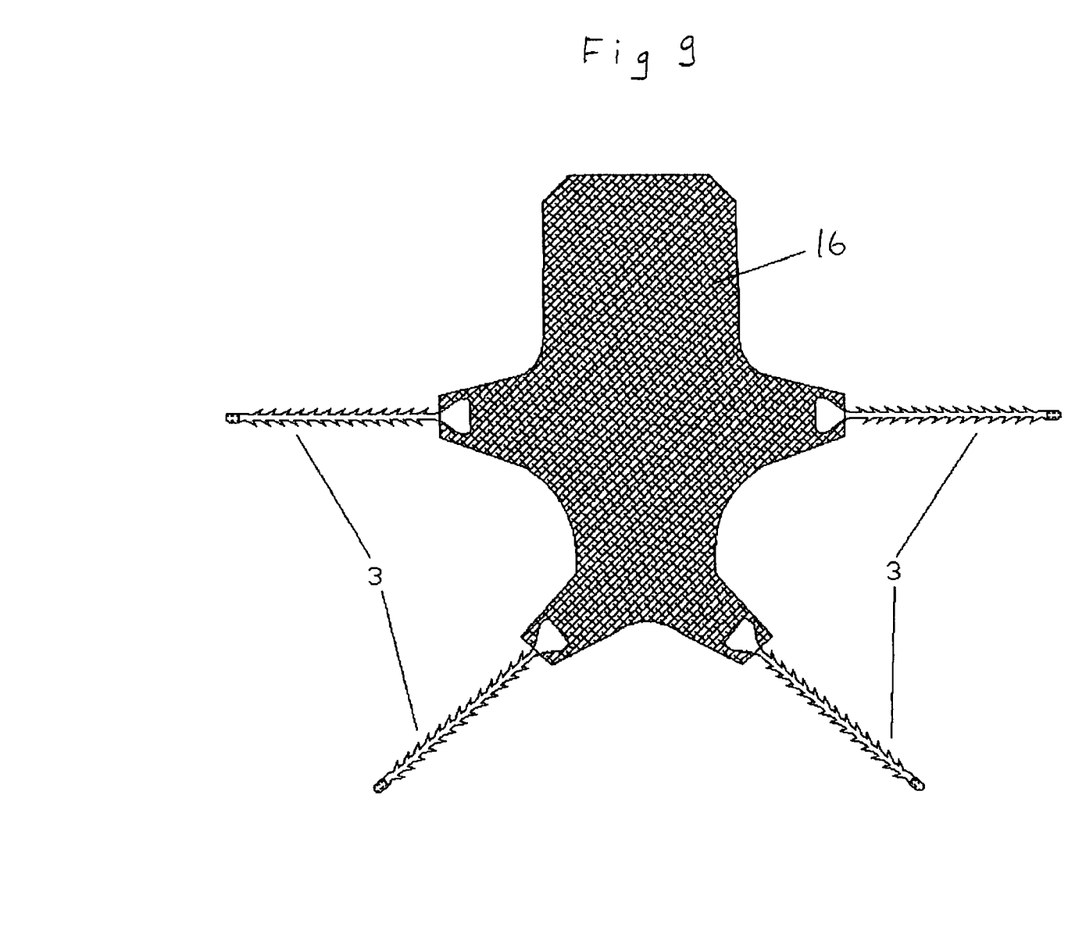
FIG. 9 is a plan view of an implant for anterior vaginal wall prolapse treatment.

As illustrated in FIGS. 8 and 9, the self-anchoring means previously described could also be used to fix other meshes or implantation devices, such as those used for the treatment of vaginal prolapse.

Self anchoring means can be used for fixing meshes 15 (FIG. 8) in rectocele and vaginal vault prolapse treatment. Meshes are supported in tissue by means of sutures or two mesh extensions or fixing tails which are implanted using long and thick needles. With this method, a mesh 15 is supported free tension between the vaginal wall and rectum by two self-anchoring tails which attach bilaterally to the sacrospinous ligament.

The two self-anchoring tails 3 of the sling constitute a system, which can be self-anchored to the obturator internus muscle. Therefore, the sling is fixed without sutures. This self-anchoring means is enough to keep the sling in its place when there is an important muscle activity and strains such as coughing.

Another use could be to fix meshes to various tissues, muscles and ligaments in the pelvic area for the treatment of vaginal anterior wall prolapse. These meshes are usually supported in the pelvic tissue by means of sutures or either mesh extensions or fixing tails. With this method, a mesh 16 (FIG. 9) is supported free tension between the vaginal wall and bladder by four self-anchoring tails 3 which attach to the obturator internus muscles—two on each side.

We are now going to describe an anatomical approach for female urinary incontinence treatment The anatomical approach of the micro sling consists in placing the mid-part mesh in mid-urethral and the self-anchoring tails anchored to the obturator internus muscle at the level of the arcus tendinous bilaterally.

The procedure is performed with the patient in the lithotomy position under local or spinal anesthesia. Two grams of first-generation of cephalosporin is administered intravenously at the time of anesthesia induction.

The steps of the surgical procedure for implanting the sling using the mini trocar 10 are the following:

- A 1 cm long vertical vaginal incision is performed at 1.5 cm from the urethral meatus. Minimal vaginal dissection is performed laterally toward the ascending ramus of the ischiopubic bone.
- The trocar awl 13 is threaded through one of the micro sling ends part 4.
- Next, the mini trocar 10 is introduced in the incision and guided by the surgeon's index finger placed at the vaginal fornix, towards the homolateral shoulder of the patient until the endopelvic fascia is perforated.
- The trocar 10 is then moved forward 2 or 3 cm into the obturator internus muscle.
- Once in place, the awl 13 is unthreaded by moving the trocar button 14 backward. Then, the trocar 10 is removed.
- The trocar awl 13 is threaded to the other end of the sling and the three above steps are repeated.
- Tension adjustment is made by placing the mesh in contact with the urethra with no tension keeping an 18 Fr Foley catheter in place.
- The vaginal incision is closed in the usual manner, the Foley catheter is removed and the patient is discharged after spontaneous voiding.

We are now going to describe, anatomical approaches for female and male faecal incontinence treatment. As illustrated in the FIGS. 10 to 12, the anococcygeal ligament 18 is attached to the tip of coccyx 20. Transverse perineal muscles 21 are attached to the ischial tuberosity 22.

Figure 10:
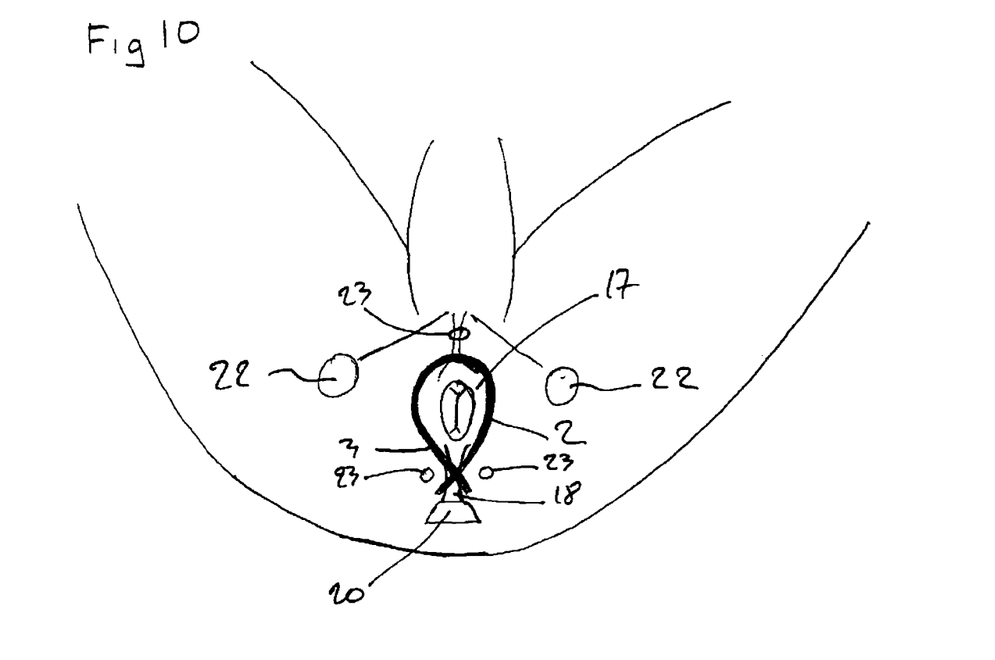
FIG. 10 is an illustration of a use of a sling in faecal incontinence treatment.
Figure 11:
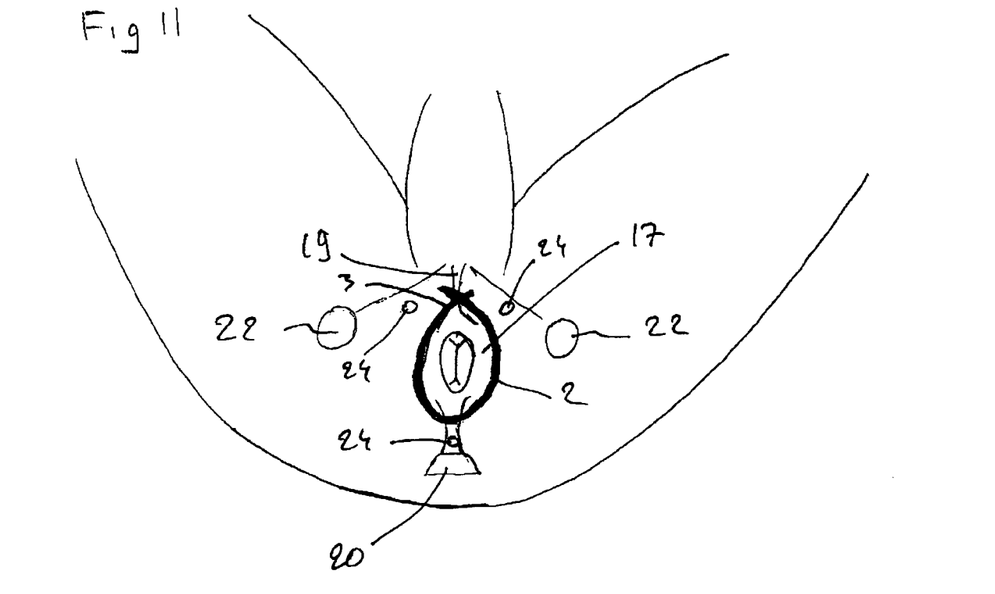
FIG. 11 is an illustration of another use of a sling for faecal incontinence treatment.
Figure 12:
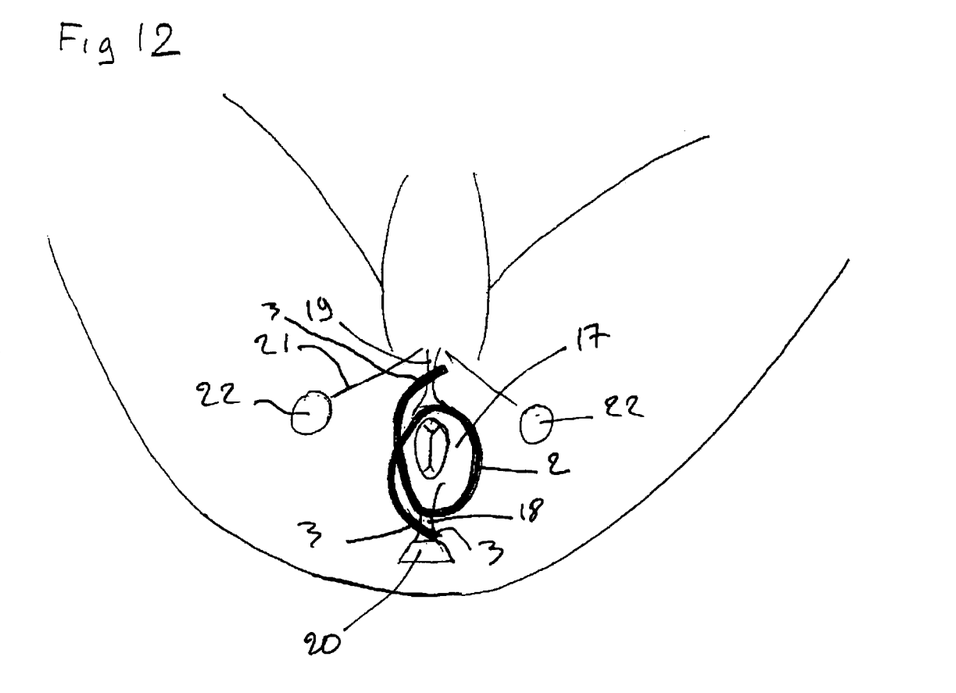
FIG. 12 is an illustration of a third use of a sling for faecal incontinence treatment.

The surgical procedure for implant this micro sling to treat fecal incontinence is an inventive low invasive surgical approach. In this case, the sling mesh 2 is supported with low tension by the external anal 17 sphincter and the self-anchoring tails 3 attach to the anococcygeal ligament 18 and/or to the central pireneal tendon 19.

The procedure where both ends of a sling is fixed to the anococcygeal ligament 18 is the following (see FIG. 10):

- A 1 cm transverse incision 23 is made at the raffe, 2 cm above the center of the anus.
- Two other incisions 23 are made laterally at 5 and 7 o'clock position regarding the anus.
- Blunt dissection is made around the external anal sphincter in all incisions.
- Using the mini trocar 10, the self anchoring tails 3 of the micro sling are introduced towards the lateral incisions 23 at each side.
- One the slings ends are exteriorized at the lateral incisions 23, the mesh 2 is put in the proper place around the anal external sphincter 17. Once the adjustment is made, the self-anchoring tails 3 are introduced through the same lateral incision 23 towards the Anococcygeal ligament 18.

Using the mini trocar 10, the end part 4 of the self anchoring tail 3 is introduced in the ligament towards the tip of the coccyx 20. Once in place the button 14 is pressed down and the self anchoring tail 3 of the sling is deployed form the mini trocar 10.

The same maneuvers are repeated on the other side, leaving the sling in a low-tension manner.

The incisions 23 are closed and prophylactic antibiotics are prescribed. Stool softener is useful for the first post-operative week.

The procedure where both ends of a sling is fixed to the to the central perineal tendon is the following (see FIG. 11):

A 1 cm transverse incision 24 is made at the raffe, 2 cm below the center of the anus.

Two other incisions 24 are made laterally at 2 and 10 o'clock position regarding the anus.

Blunt dissection is made around the external anal sphincter in all incisions 24.

Using the mini trocar 10, the self anchoring tails 3 of the micro sling are introduced towards the lateral incisions at each side.

One the slings ends are exteriorized at the lateral incisions 24, the mesh 2 is put in the proper place around the anal external sphincter 17. Once the adjustment is made, the self-anchoring tails 3 are introduced through the same lateral incision 24 towards the central perineal tendon 19.

Using the mini trocar 10, the end part 4 of the self anchoring tail 3 is introduced in the ligament. The procedure follows as previously described.

Another surgical approach is a mixture of the previous procedures, in which one of self anchoring tails 3 anchor in the anococcygeal ligament 18 and the other in the central perineal tendon 19. The central mesh of micro sling is surrounding the anal external sphincter 17. This approach is indicated for the cases of severe faecal incontinence because a circumferential coaptation of sling around the external anal sphincter 17 takes place.

The invention claimed is:

1. An implantation system comprising a sling for urinary and faecal incontinence treatment and an implantation tool said sling consisting of: a mid-part having a length of 20 to 100 mm, two fixing tails each comprising an anchoring means, an elongated part fixed to the mid-part, and an end part fixed to the elongated part, the end part including a connection means connectable to a tool, at least one fixing tail being an autofixing tail including self-anchoring means, wherein the elongated part is substantially flat and the end part is axially disconnectable from the tool, the substantially flat elongated part of the autofixing tail consisting of substantially flat self-anchoring means, wherein the elongated part of the sling has a thickness of 0.3 to 1 mm, the end part consists of a butting surface substantially perpendicular to a distal portion of the elongated part with a chamfered or rounded edge on a surface distal to the elongated part, the connection means of the end part is within the butting surface and consists of a fixing hole, substantially parallel to the distal portion of the elongated part, said implantation tool comprising a cannula, an awl axially moveable inside the cannula between a protruding and a non protruding position, and an actuator of the awl, wherein the awl has a diameter adapted to enter into the fixing hole of the sling, the cannula being designed for not entering into said fixing hole, the awl comprising a tip with a stop, the stop having a diameter that is larger than the awl diameter, the fixing hole has a diameter smaller than the stop diameter of the awl tip of the tool and elastically deformable to allow the awl tip to cross along the fixing hole, the actuator being designed such that, in the protruding position, the stop protrudes from the end part of the sling, wherein the mid part of the sling is a mesh comprising a main part substantially rectangular, and two side tongues, extending from the two ends of a short side of the main part in two substantially perpendicular directions, a fixing tail extending from each of the side tongues, wherein the main part of the mesh of the sling comprises two lateral tongues extending in a direction substantially perpendicular to a long side of the main part, a fixing tail extending from each lateral tongue, and wherein the fixing tails consist of a fixing pad fixed onto only one surface of the mid part of the sling.

2. The implantation system according to claim 1, wherein the end part and the elongated part of the fixing tail of the sling are made of the same material.

3. The implantation system according to claim 1, wherein the self anchoring means of the sling comprises two longitudinal lines, of thorn-like projections radially extending from a central part of the tail and having a triangular or a rectangular or a trapezoidal or a curved shape.

4. The implantation system according to claim 1, wherein the self anchoring means of the sling comprises substantially rigid sub units.

5. The implantation system according to claim 1, wherein the width of the tails of the sling are between 2 to 5.5 mm.

6. The implantation system according to claim 1, wherein each of the fixing tails of the sling are autofixing tails provided with self-anchoring means.

7. The implantation system according to claim 1 wherein the sling is a sling mesh and is supported in a low tension by the external sphincter and self anchoring means are adapted to be attached to the anococcygeal ligament.

8. The implantation system according to claim 1, wherein the sling is a sling mesh and is supported in a low tension by the external sphincter and self anchoring means are adapted to be attached to the central perineal tendon.

9. The implantation system according to claim 1, wherein the fixing tails and fixing pads are made of a thermo-hardened theremoplastic material that is fixed to the mesh of the mid-part.

10. An implantation method of implanting a sling into a soft tissue using an implantation system according to claim 1, comprising a preliminary step of attaching an end part of the sling to the tool end in such way that the attachment holds the sling at least in a tensile direction of the sling, and a further step of pushing the tool and the end part of the sling into the soft tissue, in order to carry the sling with the tool side by side, wherein the preliminary attachment is such that it holds the sling end part in any direction, the step of pushing the tool or the trocar being performed up to a place where the sling end part reaches its final location into the soft tissue, and therein the tool is further detached from the sling end part without either pulling or pushing said sling end part, and the sling and the implantation tool are introduced through the same incision and the tool is removed through the same incision again.

* * * * *